(12) United States Patent
Chougrani et al.

(10) Patent No.: US 7,900,517 B2
(45) Date of Patent: Mar. 8, 2011

(54) SYSTEM AND METHOD FOR INSPECTING A PIPELINE WITH ULTRASOUND

(75) Inventors: Khalid Chougrani, Delft (NL);
Frederik Hendrik Dijkstra, Oudenbosch (NL); Cesar Justino Buque, Geesthaacht (DE); Robert van Agthoven, Berkel en Rodenrijs (NL)

(73) Assignee: Rontgen Technische Dienst B.V., Rotterdam (NL)

( * ) Notice: Subject to any disclaimer, the term of this patent is extended or adjusted under 35 U.S.C. 154(b) by 79 days.

(21) Appl. No.: 12/457,597

(22) Filed: Jun. 16, 2009

(65) Prior Publication Data
US 2010/0313665 A1    Dec. 16, 2010

(51) Int. Cl.
*A61B 5/04* (2006.01)

(52) U.S. Cl. ............... 73/623; 73/592; 73/598; 73/625; 73/633

(58) Field of Classification Search ............ 73/623, 73/625, 628, 633, 592, 598, 644, 865.8
See application file for complete search history.

(56) References Cited

U.S. PATENT DOCUMENTS

| | | | | |
|---|---|---|---|---|
| 4,170,891 A | * | 10/1979 | Elsner | 73/1.83 |
| 4,559,825 A | * | 12/1985 | Martens | 73/622 |
| 4,991,441 A | * | 2/1991 | Nottingham et al. | 73/633 |
| 5,317,387 A | * | 5/1994 | Van Hengel et al. | 356/625 |
| 6,497,150 B1 | * | 12/2002 | Kruzic | 73/611 |
| 7,082,822 B2 | * | 8/2006 | Harthorn et al. | 73/152.57 |
| 7,104,125 B2 | * | 9/2006 | Harthorn et al. | 73/152.57 |
| 7,168,322 B2 | * | 1/2007 | Bardoux et al. | 73/588 |
| 7,234,347 B2 | * | 6/2007 | Harthorn et al. | 73/152.57 |
| 7,552,631 B2 | * | 6/2009 | Harthorn et al. | 73/152.57 |

FOREIGN PATENT DOCUMENTS

GB    2 255 825    11/1992

* cited by examiner

*Primary Examiner* — Jacques M Saint Surin
(74) *Attorney, Agent, or Firm* — Jacobson Holman PLLC

(57) ABSTRACT

A system for inspecting a pipeline with ultrasound, provided with a transport device arranged to move in a transport direction through the pipeline, a plurality of transducers and a transmitting and receiving device connected with the transducers. The transducers and the transmitting and receiving device are mounted on the transport device. The transducers are provided with a first set of transducers, a second set of transducers and a third set of transducers. The system is arranged to move the first set of transducers, the second set of transducers and the third set of transducers in a tangential direction with respect to the transport direction along an interior wall of the pipeline. The system is arranged to bring the transducers of the first set, the second set and the third set into contact with the interior wall of the pipeline during the performance of a measurement.

34 Claims, 4 Drawing Sheets

SYSTEM AND METHOD FOR INSPECTING A PIPELINE WITH ULTRASOUND

This invention relates to a system for inspecting a pipeline possibly filled with a fluid such as water and/or oil with ultrasound, provided with a transport device arranged to move in a transport direction of the transport device through the pipeline and a plurality of transducers for transmitting ultrasound and for receiving reflections and/or diffractions of the transmitted ultrasound on a wall of the pipeline for performing a measurement, and a transmitting and receiving device connected with the transducers for activating the transducers for transmitting the ultrasound and for generating receive signals respectively representing ultrasound including reflections and/or diffractions received with the transducers, the transducers and the transmitting and receiving device being mounted on the transport device.

The invention further relates to a method for inspecting a pipeline possibly filled with a fluid such as water and/or oil with such a system.

Such a system and method are known per se from inter alia GB 2255825.

The known apparatus may be provided with a combination of tandem, single-shear wave and dual 0° transducers.

These transducers can be rotated by the apparatus to inspect an interior of the pipeline, for instance in the vicinity of a weld.

A problem of the known system is that it proves not to be possible to discover different types of cracks in the wall of the pipeline, in particular in a weld of the pipeline. In particular, it is difficult to detect cracks extending in radial and/or axial direction. Nor is it possible to properly determine the size of such cracks.

The object of the invention is to provide a system which obviates the disadvantages mentioned.

The system according to the invention is accordingly characterized in that the transducers are provided with a first set of transducers which comprises at least two phased array transducers staggered with respect to each other at least in the transport direction, a second set of transducers which comprises at least two transducers staggered with respect to each other in the transport direction for performing a TOFD measurement, and a third set of transducers which comprises at least two transducers staggered with respect to each other in the transport direction for performing a measurement with creep waves, wherein the system is arranged to move the first set of transducers, the second set of transducers and the third set of transducers in a tangential direction with respect to the transport direction along an interior surface of the wall of the pipeline and wherein the system is arranged to bring the transducers of the first set, the second set and the third set into contact with the interior surface of the pipeline during the performance of the measurement.

Through the combined provision of the first set of transducers, the second set of transducers and the third set of transducers, while the system is arranged to move these transducers in tangential direction with respect to the transport direction along the interior surface of the pipeline, and while the system is arranged to bring the transducers of the first set, the second set and the third set into contact with the interior surface of the pipeline during the performance of the measurement, it proves possible to perform a highly accurate inspection of the pipeline. Here, different types of cracks can be detected with great accuracy and moreover, if so desired, the size of these cracks can be determined with great accuracy.

The first set of transducers, the second set of transducers and the third set of transducers provide different kinds of measuring methods which supplement each other and partly overlap and hence provide redundancy. Thus, in combination, a highly accurate inspection is enabled. This is further improved in that the transducers of the first set, the transducers of the second set and the transducers of the third set are in contact with the interior surface of the pipeline during the performance of a measurement. When the pipeline is filled with a fluid such as water and/or oil, this fluid has as an advantage that a good acoustic coupling is obtained between the transducers of the first set, second set and third set on the one hand and the wall of the pipeline on the other hand. If the pipeline is not filled with such a fluid, the device may be arranged to provide such a fluid between these transducers and the wall of the pipeline for obtaining a good acoustic coupling between the wall of the pipeline on the one hand and the first, second and third set of transducers on the other hand. Also if the pipeline is not filled with such a fluid, the transducers may be of a type which can perform measurements while being in contact with the wall of the pipeline such as EMAT, Laser UT and Airborne UT.

In particular, it holds that the system is arranged to move the first set of transducers, the second set of transducers and the third set of transducers in a tangential direction with respect to the transport direction along the interior surface of the pipeline while these transducers are in contact with this interior surface. This enables continuous measurement as the transducers move in tangential direction along the interior surface of the pipeline. In particular, it holds that for the at least two transducers of the first set of transducers, the second set of transducers and the third set of transducers, it holds that they are staggered over a distance which is in line with regulations and codes. The distance in the transport direction between two transducers depends amongst others on the thickness of the wall and the angles of the transducers relative to the wall. This distance can be determined by a person skilled in the art on the bases of codes, regulations and skills. In a majority of the codes it is regulated that for TOFD the main axes of the beams should cross each other at a distance from the inner surface of the wall which is ⅔ of the thickness of the wall. For Pulse-echo, tandem and sector scan, the position of the transducer follows from the angle of the bundle transmitted by the transducer in combination with the thickness of the wall and the expected position and orientation of a defect in the wall. For creep waves the maximum travelling distance is limited so that the distance to the weld may not be too large (typically 50 mm maximum).

Such a system is particularly suitable for inspecting a weld because in each case the at least two transducers of the first set, the second set and the third set can be placed on opposite sides of a weld for performing measurements.

In particular, it holds furthermore that the system is further provided with a fourth set of transducers and a fifth set of transducers, which transducers are each fixedly connected with the transport device, wherein the fourth set of transducers comprises at least two transducers which have a mutually different tangential position and which are so mounted that they transmit ultrasound in a radial direction with respect to the transport direction and wherein the fifth set of transducers comprises at least two transducers which have a mutually different tangential position and which are so mounted that they transmit ultrasound in a radial direction with respect to the transport direction, wherein the transducers of the fourth set on the one hand and the transducers of the fifth set on the other hand are separated at a distance from each other in the transport direction. Using the fourth set of transducers and the fifth set of transducers, for instance a distance measurement can be performed, from a transducer as far as the wall (as far as the interior surface and/or as far as the exterior surface of the pipeline). Also, a wall thickness measurement can be performed. In this way, when the transport device moves through a pipeline, a weld can be detected in a simple manner because at the position of the weld the wall thickness of the pipeline increases and/or the distance to the interior surface decreases. If in this way a weld is found, the transducers of the first set, the second set and the third set can be placed, for instance, on opposite sides of the weld, as discussed hereinabove. It is also possible, using the fourth and fifth sets of transducers, to determine a position of the transport device with respect to the pipeline. In this way, for instance, coincidence of an axial axis of the transport device with an axial axis of the pipeline may be verified and/or corrected.

In particular, it holds that, in use, with the first set of transducers, , a TANDEM measurement and a Pulse-echo measurement, respectively, is performed. A series of TANDEM measurements may be carried out so that the full thickness of the weld within a zone is inspected. In addition to this series, at least one Pulse-echo measurement is carried out. If a TOFD measurement is carried out with the second set of transducers the complete volume to be inspected is inspected by means of a single pulse. The information of a defect can be determined on the basis of time differences between the moments at which diffractions of the single pulse are received by means of a transducer.

According to a highly advanced embodiment, it holds that, in use, with the first set of transducers also a Sector-scan measurement is performed. Such a Sector-scan measurement is in fact a representation which combines multiple individual (pulse echo) measurements. These individual measurements are displayed on a screen 'stacked' together, resulting in a 2-dimensional cross section of the volume under examination. Amplitude is usually shown with a colour palette, usually rainbow. Remember this presentation may seem 'movie like' (simultaneous) but in fact it is sequential i.e. one measured beam at once. Note that the term Sector-scan is used for different setups for the individual beams:

Parallel or linear scans, sometimes even referred to as Linear sector, where all individual beams have the same direction but have different index points.

Sectorial or azimuthal scans, sometimes referred to as Sectorial sector, where all individual beams have a different direction but have, at least substantially, the same index point.

Different types of measurements or scans can be performed with the first set of transducers which are phased array transducers. Such variants are each understood to fall within the term sector scan and within the framework of the invention. In particular, it holds furthermore that the system is further provided with a signal processing unit which is connected with the transmitting and receiving device for combined processing of receive signals coming from the first set of transducers, the second set of transducers and the third set of transducers for inspecting the pipeline, in particular for detecting a crack and/or determining the size of a crack in the wall of the pipeline and/or in a weld of the pipeline.

Preferably, it holds here that the signal processing unit is separated from the transport device. In particular, it holds furthermore that the signal processing unit, in use, on the basis of receive signals coming from the fourth and fifth set of transducers, determines a position of the transport device with respect to the pipeline and/or determines a thickness of the wall of the pipeline. Preferably, it holds here that the signal processing unit is arranged to locate a weld in the pipeline on the basis of receive signals coming from the fourth and/or fifth set of transducers.

The method according to the invention is characterized in that
a. the transport device is transported in the transport direction through the pipeline to a part of the pipeline to be inspected and is stopped at the part to be inspected;
b. the transducers of the first set, the transducers of the second set and the transducers of the third set are brought into contact with an interior surface of a wall of the pipeline;
c. using the transducers of the first set, ultrasound is transmitted and receive signals are generated while the transducers of the first set are in contact with the interior surface of the pipeline;
d. using the transducers of the second set, ultrasound is transmitted and receive signals are generated while the transducers of the second set are in contact with the interior surface of the pipeline;
e. using the transducers of the third set, ultrasound is transmitted and receive signals are generated while the transducers of the third set are in contact with the interior surface of the pipeline;
f. the first set of transducers, the second set of transducers and the third set of transducers are moved in a tangential direction with respect to the transport direction along the interior surface of the pipeline.

The invention will presently be further elucidated with reference to the drawing. In the drawing.

Figure 1:
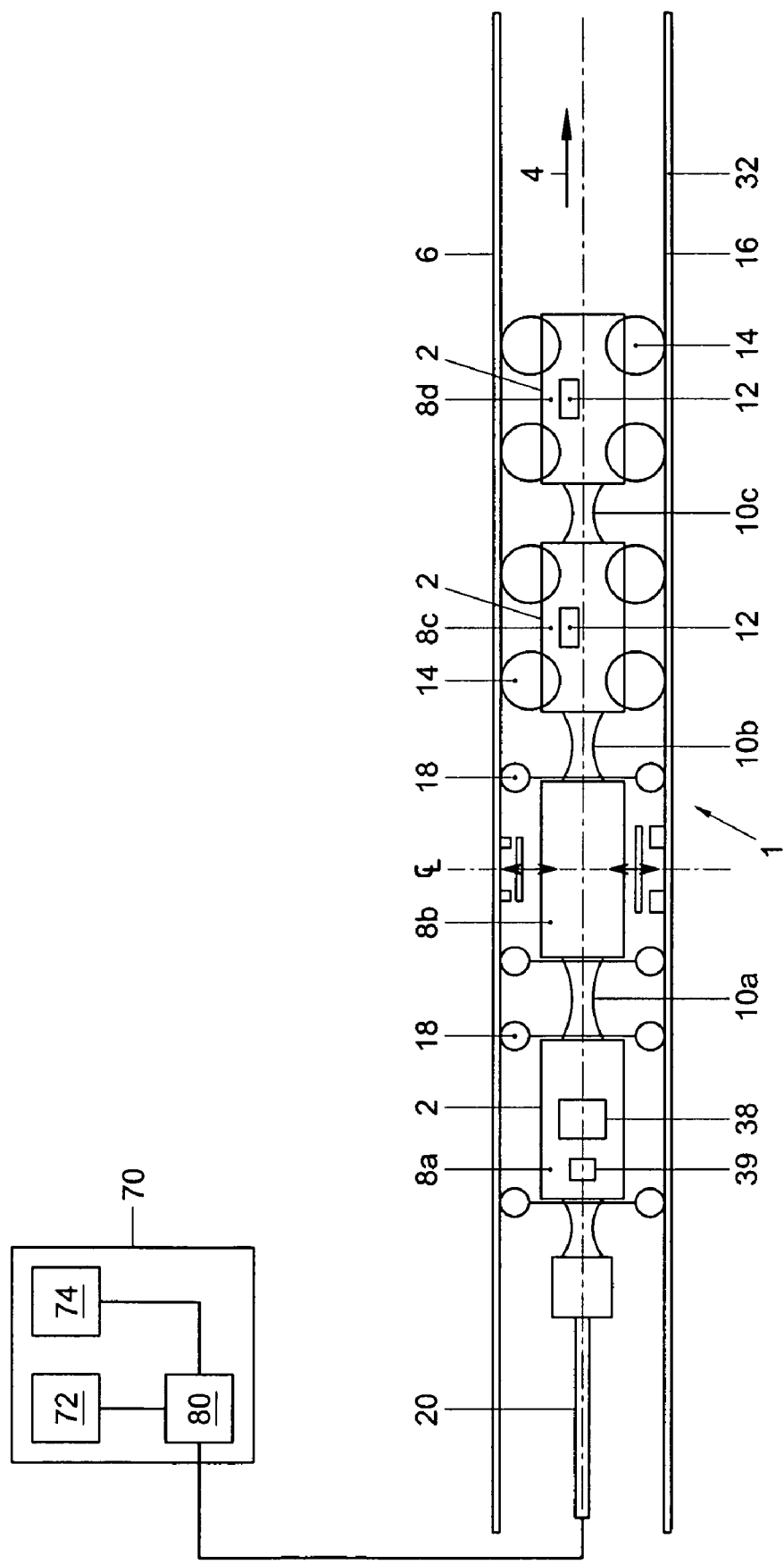
FIG. 1 shows a possible embodiment of a system according to the invention.
Figure 2A:
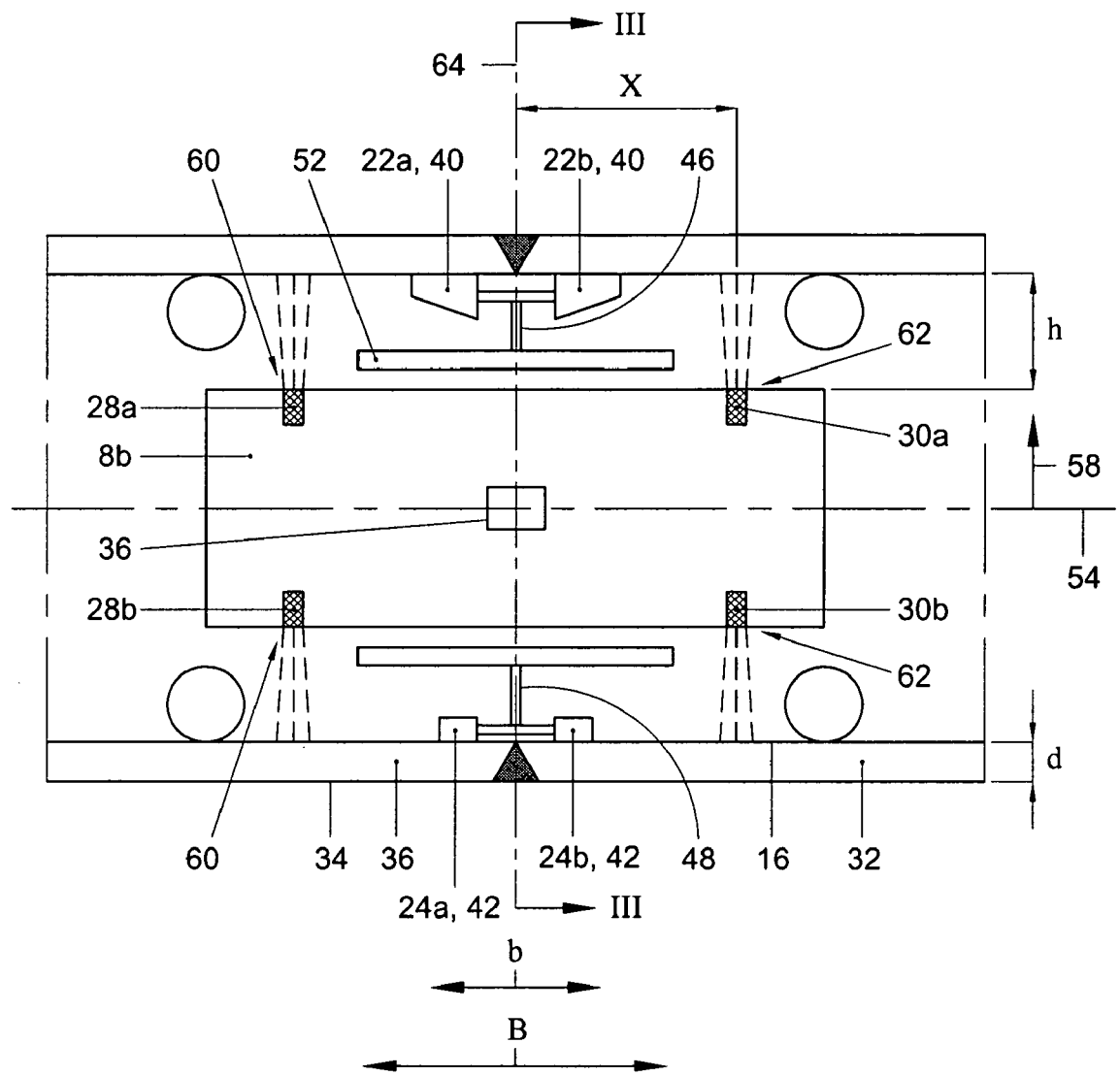
FIG. 2a shows a cross section of the system according to FIG. 1 along line 2a of FIG. 3.
Figure 2B:
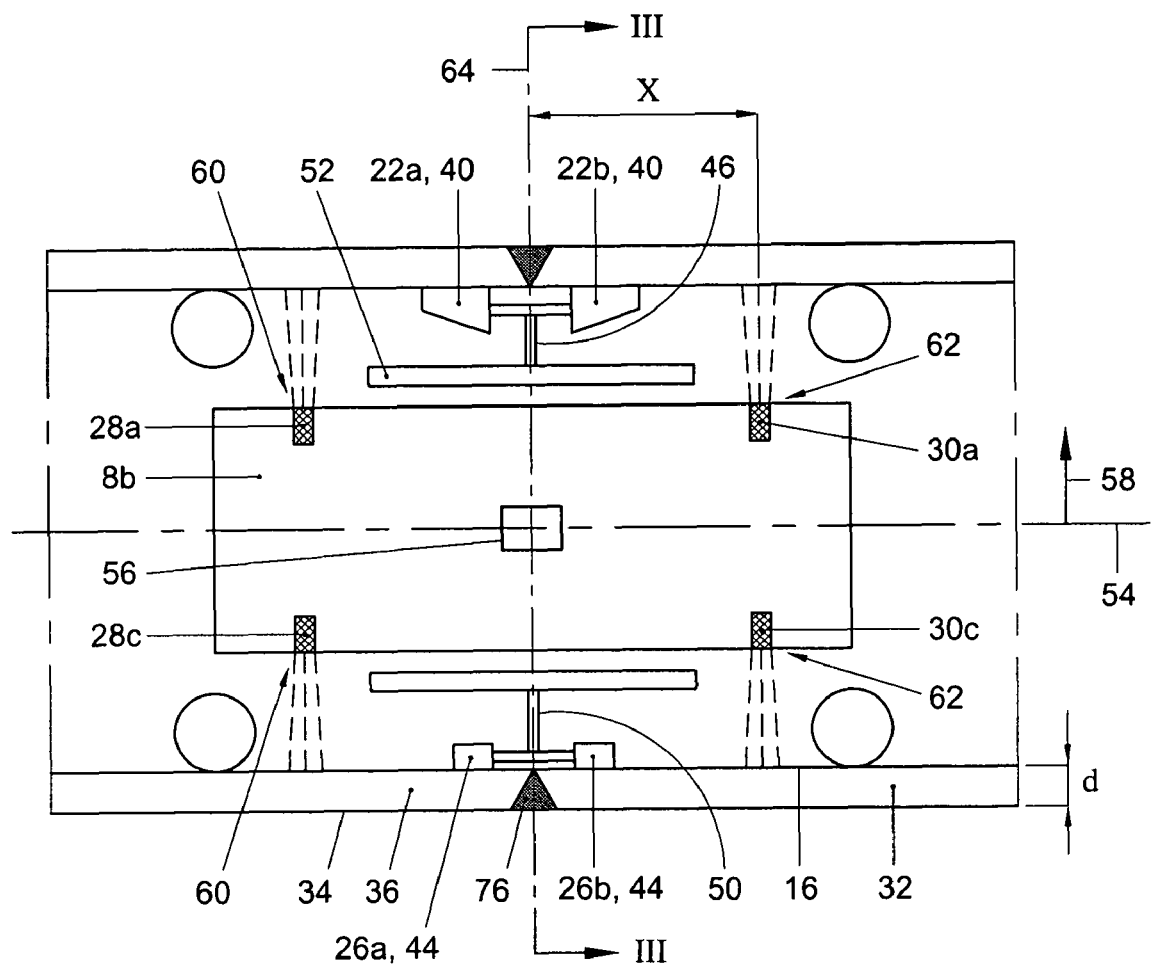
Figure 3:
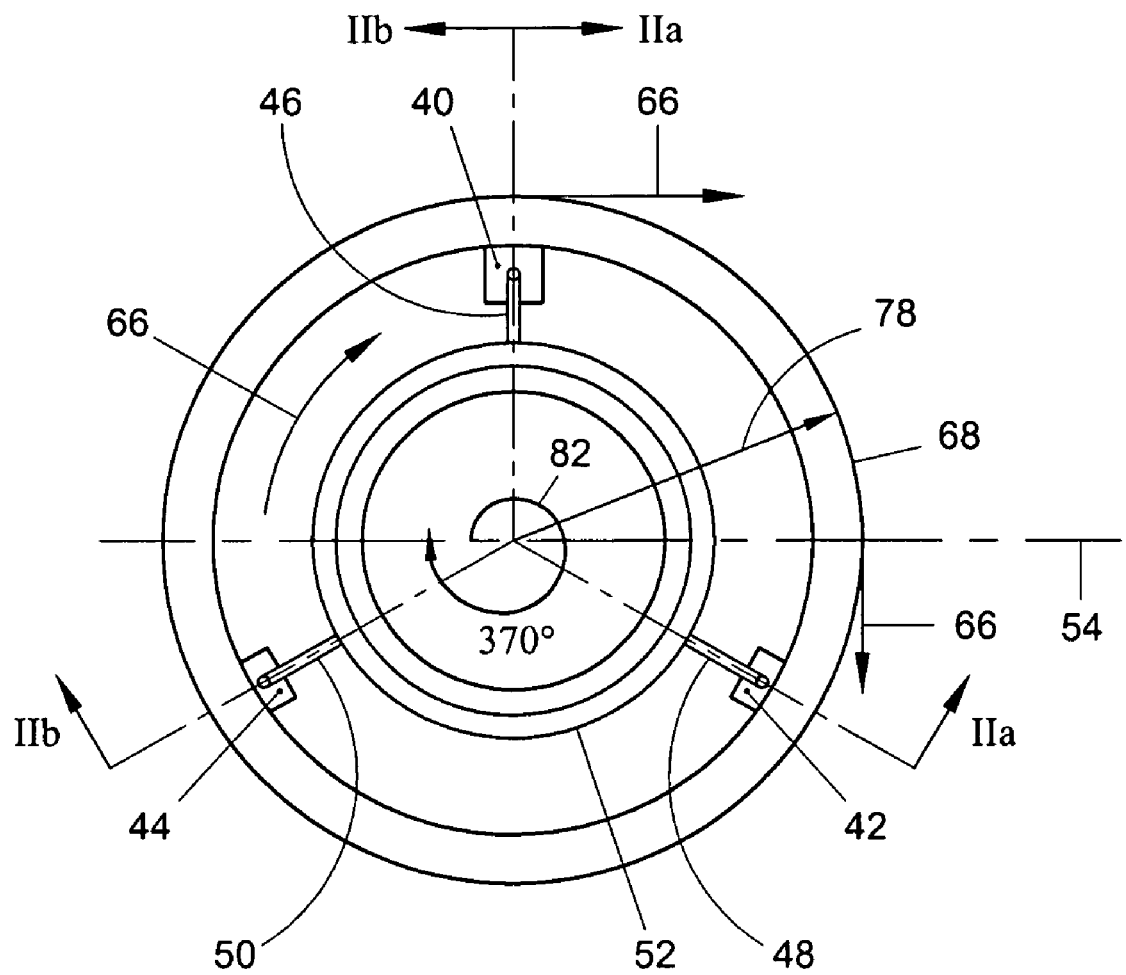

FIG. 2b shows a cross section of the system according to FIG. 1 along line 2b-2b of FIG. 3; and FIG. 3 shows a cross section of the system according to FIG. 1 along the line 2-2 of FIGS. 2a and 2b.

In FIG. 1, reference numeral 1 designates a system for inspecting a pipeline possibly filled with a fluid such as water and/or oil with ultrasound. The system is provided with a transport device 2 which is arranged to move in a transport direction 4 through a pipeline 6. In this example, the pipeline is filled with water. The transport device is provided with a first transport module 8a, a second transport module 8b, a third transport module 8c, and a fourth transport module 8d. The transport modules 8a and 8b are connected with each other through a flexible coupling 10a. The transport modules 8b and 8c are connected with each other through a flexible coupling 10b, and the transport modules 8c and 8d are connected with each other through a flexible coupling 10c. The flexible couplings 10a, 10b and 10c are each designed to flex so that the system 1 can travel through curves in the pipeline. However, in this example, these couplings are each rigid in their longitudinal direction so that the distances between the modules 8a, 8b and 8c is fixed. This is advantageous for positioning the modules and more particularly certain parts of the modules such as transducers on a desired location in the pipeline.

Transport modules 8c and 8d are each provided with a motor 12 which drive wheels 14 of the transport modules of the transport device 2 through the pipeline 6. To this end, the wheels bear on an interior surface 16 of the pipeline. The transport modules 8a and 8b are also provided with wheels 18 which bear on the interior surface 16, but these wheels are not driven. The transport module 8a is provided with electronics, to be further discussed below, which communicates with a signal line 20 passing outside the pipeline. The transport module 8b and hence the transport device 2 is provided with a plurality of transducers 22a, 22b, 24a,24b,26a,26b, 28a-28c and 30a-30c for transmitting ultrasound and for receiving reflections of transmitted ultrasound on a wall 32 of the pipeline. Wall 32 of the pipeline is herein understood to mean the interior surface 16 of the pipeline but also the exterior surface 34 of the pipeline as well as the material 36 of the wall of the pipeline present between the interior surface 16 and the exterior surface 34. As the pipeline is filled with a fluid such as, in this example, water (and/or oil is also possible), this fluid has as an advantage that a good acoustic coupling is obtained between the transducers of the first set, second set and third set on the one hand and the wall of the pipeline on the other hand. If the pipeline is not filled with such a fluid, the device may be arranged to provide such a fluid between these transducers and the wall of the pipeline for obtaining a good acoustic coupling between the wall of the pipeline on the one hand and the first, second and third set of transducers on the other hand. Alternatively transducers such as EMAT, Laser UT and Airborne UT may be used which do not require a coupling fluid.

Included in the transport module 8a is a transmitting and receiving device 38 which communicates with the signal cable 20 on the one hand and which communicates with each of the transducers on the other hand. The transmitting and receiving device is arranged for activating the transducers for transmitting the ultrasound using the transducers and for generating receive signals respectively representing ultrasound received with the transducers, including reflections on a pipeline of ultrasound transmitted with the ultrasonic transducers.

The transducers comprise a first set of transducers 40 which comprises the at least two phased array transducers 22a,22b staggered with respect to each other in the transport direction. Further, the system is provided with a second set of transducers 42 which comprises at least two transducers 24a and 24b staggered with respect to each other in the transport direction 4, for performing a TOFD measurement. Further, the system is provided with a third set of transducers 44 which comprises at least two transducers 26a, 26b staggered with respect to each other in the transport direction, for performing a measurement with creep waves.

The first set of transducers 40 is connected with the transport device 2 via a rod 46. The second set of transducers 42 is connected with the transport device 2 through a rod 48. Further, the third set of transducers 44 is connected with the transport device 2 through a rod 50. In particular, it holds here that the rods each have a free end connected with a sleeve 52 connected with the transport module 8b for rotation around an axial axis 54 of the transport device 2. The transport module 8b is provided with a motor 56, designated schematically in the drawing, to rotate the sleeve 52 around the axial axis 54. The rod 46 is made of telescopically movable design so that the first set of transducers 40 can be moved outwards in radial direction until they abut against the interior surface 16. Entirely analogously, also the rod 48 is of length-adjustable design, so that the second set of transducers can be pressed against the interior surface 16 when the length of the rod 48 is augmented. Also the length of the rod 50 is variable to allow the third set of transducers to be pressed against the interior surface 16. Evidently, the length of the rod 46, 48, 50 can be reduced again as well, for respectively moving the first set of transducers, the second set of transducers and the third set of transducers in radial direction away from the interior surface 16. Alternative means such as arms provided with controllable hinges for positioning the transducers are also possible. In this example, the length of the rods 46, 48 and 50, respectively, is settable using control signals which are applied to the transport device 2 via the signal cable 20.

The system in this example is further provided with a fourth set of transducers 60 and a fifth set of transducers 62. The fourth set of transducers and the fifth set of transducers are ach fixedly connected with the transport device 2. The fourth set of transducers comprises at least two, and in this example three, transducers 28a, 28b, 28c, which have a mutually different tangential position with respect to the axial axis 54 and which are so mounted that they transmit ultrasound in a radial direction 58 with respect to the transport direction, in the direction of the interior surface. As can be seen in FIGS. 2a and 2b, the transducers 28a-28c of the fourth set are distributed at least substantially uniformly along a circle, with a plane of the circle being perpendicular to the axial axis 54. In this example, it holds that the fifth set of transducers 62 is provided with at least two, and in this example three, transducers 30a-30c, which are likewise distributed in tangential direction at least substantially uniformly along a circle, with a plane of this circle being also directed perpendicular to the axial axis 54.

As appears from FIG. 2a, 2b and FIG. 3, it holds furthermore that the middle between the first set of transducers 40, the middle between the second set of transducers 42, the middle between the third set of transducers 44 are each situated, at least substantially, in a same flat plane 64, which is directed perpendicular to the transport direction 4 of the transport device 2. Further, it holds that the first set of transducers, the second set of transducers and the third set of transducers are distributed in the tangential direction 66 at least substantially uniformly along a circle 68.

The invention in this example is further provided with an operating console 70 which is placed outside the pipeline and is connected with the signal cable 20. The console is provided with a display 72 and an input unit 74 which is provided, for instance, with a number of buttons for operating the transport device 2. The display and the input unit are connected with a signal processing unit 80 of the console 70.

The system described up to this point works as follows. For inspecting a weld 76 of the pipeline 6, the transport device is introduced into the pipeline 6. Then, using the input unit 74, a signal is supplied to the signal line 20 which results in the motors 12 being started, so that the transport device starts to move in the transport direction 4 through the pipeline. At the same time, the fourth and the fifth set of transducers are activated, whereby each transducer transmits ultrasound in a radial direction 78. With these transducers, the presence of the weld 76 can be detected. In this example, the ultrasound is transmitted in the form of pulses. These pulses will reflect on the interior surface 16 and the exterior surface 34 of the pipeline. In this way, in a manner known per se, a thickness d of the wall of the pipeline and/or the standoff h (see FIG. 2a) can be determined by each of the transducers of the fourth set of transducers and the fifth set of transducers. As the thickness d of the pipeline at a weld will be different, typically thicker, and/or the standoff distance between the transducer and the inner wall will be typically smaller, the position of a weld can be determined in this way. During transportation of the transport device through the pipeline, the weld 76 will be determined first by each of the transducers of the fifth set. The transmitting and receiving device generates receive signals which are applied to the signal processing unit 80 of the operating console. The signal processing unit processes the receive signals and images them on the display 72. On the basis of this image of the receive signals, an operator can determine the thickness d of the wall of the pipeline and/or the standoff and thus the position of the weld. When the weld has thus been detected, an operator will operate the transport device by way of the input unit, such that the transport device, after detection of the weld, is moved further over a distance X in the transport direction 4. The result is that the transducers 22*a*, 24*a*, and 26*a* come to lie on, in this example, a left-hand side of the weld 76, while the transducers 22*b*, 24*b* and 26*b* come to lie on a right-hand side of the weld 76. To this end, a distance B between the first transducers 22*a* and the transducers 22*b* of the first set is greater than an internal width b of the weld. The same holds for the distance between the transducers 24*a* and 24*b* and a distance between the transducers 28*a* and 28*b*. During the above-mentioned movement of the transport device through the pipeline the rods 46, 48, 50 are in a shortened condition so that the transducers of the first set, second set and third set do not touch the interior surface 16. The pipeline may for instance be filled with water or oil. It is also possible, however, that it is still empty.

In this example, the transport device is thus stopped, such that the transducers of the first set, second set and third set take up the above-mentioned position with respect to the weld. Next, the operator will so operate the transport device that the rods 46, 48 and 50 proceed to move the transducers of the first set, the second set and third set in the radial direction 78 outwardly until the transducers of the first set, second set and third set are pressed against the interior surface 16. Next, an operator will activate the transmitting and receiving device 38 so that the transducers of the first set transmit ultrasound and so that with the transducers of the first set and the transmitting and receiving device receive signals are generated while the transducers of the first set are in contact with the interior surface of the pipeline. Also, using the transducers of the second set, an ultrasound is transmitted and receive signals are generated while the transducers of the second set are in contact with the interior surface of the pipeline. Also, using the transducers of the third set, ultrasound is transmitted and receive signals are generated while the transducers of the third set are in contact with the interior surface of the pipeline. The receive signals are each applied via the signal cable 20 to the signal processing unit 80. It is possible that the system is further provided with at least one A/D-converter 39 via which the transmitting and receiving device 38 is connected with the signal processing unit 80 wherein the A/D-converter is mounted on the transport device (as shown in FIG. 1) or is separate from the transport device. The signal processing unit ensures that the relevant information about the receive signals is displayed on the display 72. In this example, the ultrasound is transmitted by the transducers of the first set, second set and third set in pulsed form. The pulse repetition frequency is for instance 1000 to 5000 Hz. The frequency and bandwidth of the transmitted ultrasound are optimized for the wall thickness and required accuracy, and also depend on the type of measurement. Typical values are for example a frequency of 7 or 8 MHz and bandwidth of 50 to 100% for the phased array transducers, frequency of 6 MHz and bandwidth of 100% for the TOFD transducers and a frequency of 5 MHz and bandwidth of 50 to 100% for the Creep wave transducers. At the same time, that is, during the period in which ultrasound is transmitted with the transducers of the first set, the second set and third set, the motor 56 is activated so that the transducers of the first set, the second set and third set start to move in the tangential direction 66 along the interior surface 16 of the pipeline. In this example, it holds for the first set of transducers that these are moved along a loop fully closed upon itself, as in this example a circle. In other words, it holds for the first set that it is moved through at least 360 degrees around the axial axis 58. In this example, while the transport device is situated at one position in the pipeline, actually more than one revolution is performed, viz. a revolution through an angle of 370 degrees (see FIG. 3).

As the transducers 24*a* and 24*b* of the second set are situated on opposite sides of the weld, a TOFD measurement can thus be performed on the weld. In this example, this means that with the transducer 24*a* an ultrasound is transmitted which is received with the transducer 24*b*. In this example, however, also with the transducer 24*b* an ultrasound is transmitted, which is received with the transducer 24*a*. However, it is also possible that, for instance, an ultrasound is transmitted with the transducer 24*a* alone and that an ultrasound is received with the transducer 24*b* alone. It is also possible that ultrasound is transmitted with the transducer 24*b* alone and that ultrasound is received with the transducer 24*a* alone.

Also, it holds in this example that with the phased array transducer 22*a*, in succession, in a manner known per se, a TANDEM measurement, a Pulse-echo measurement and a Sector-scan is carried out. Also, it holds that with the transducer 22*b*, in succession, a TANDEM measurement, a Pulse-echo measurement and a Sector-scan is carried out. Also, it holds in this example that with the transducer 26*a* a creep wave is transmitted, which propagates in a direction of the transducer 26*b* along the interior surface 16.

Any reflections of this creep wave, in turn, are received by the transducer 26*a*. Also, the creep wave is received by the transducer 26*b*. This creep wave, too, is transmitted in pulses. Also, in this example the transducer 26*b* transmits a creep wave in pulsed form in the direction of the transducer 26*a*. Any reflections are received with the transducer 26*b*. The creep wave transmitted by the transducer 26*b* is also received with the aid of the transducer 26*a*. All this is carried out in such a manner that when a sound pulse is being transmitted with the transducer 26*a*, no sound pulse is being transmitted by the transducer 26*b* and vice versa. This also applies to the transducer pair 22*a* and 22*b* (phased array transducers). This does NOT apply for the probe pair 24*a* and 24*b* (TOFD) because the TOFD measurements works with one probe transmitting and the other probe receiving the pulse.

The receive signals thus generated with each of the transducers are (before or after digitalization, depending on whether or not an A/D-converter is added to the system 1) applied via the line 20 to the signal processing unit 80. In the example, while ultrasound is being transmitted and received with the transducers of the first set, the second set and third set, at the same time the motor 56 is activated so that the transducers are moved in radial direction along the weld for making at least a complete circumferential scan. In this example, with the first set of transducers, further a sector scan measurement, known per se, is performed. The signal processing unit which is connected with the transmitting and receiving device is arranged for combined processing of receive signals coming from the first set, the second set and the third set of transducers for inspecting the pipeline. In particular, this involves detecting a crack and/or determining the size of a crack in the wall of the pipeline and/or in a weld of the pipeline. At the same time, the signal processing unit will determine a position of the transport device with respect to the pipeline on the basis of receive signals coming from the fourth and fifth set of transducers. In fact, with the help of each of the transducers of the fourth set and fifth set a distance from for instance the interior surface 16 and/or the exterior surface 34 to such a transducer can be determined. It follows that when this information for each of these transducers is processed in combination, a position and orientation within the pipeline of the transport device, in this example of the module 8*b*, with respect to the pipeline may be determined.

The combined processing of the receive signals of the first set, the second set and third set can be carried out in various ways. Thus, the receive signals may each be represented on the display in a manner known per se. The receive signals which are each of a different type supplement each other and also have a partial overlap of information. It appears that in this way very reliable information is obtained about cracks in the weld. The described embodiment is optimized for detection and sizing of cracks generally perpendicular to the pipe surface and generally in circumferential (tangential) direction. For detection and possibly sizing of cracks with different orientation additional probes with beam orientations in other directions than the axial direction of the pipe can be used, as known to the person skilled in the art. Here, it is possible that a part of signal processing is carried out automatically with the help of the signal processing unit 80.

In this example, using the transducers of the first set, the second set and third set, an ultrasound is transmitted as these transducers move in tangential direction 66 along the interior surface of the pipeline continuously. The combination of pulse repetition frequency and transducer speed in tangential direction should be such that the tangential distance between successive measurements is smaller than the beam width in tangential direction, so that the beams of the successive measurements overlap, for each ultrasonic beam. However, it is also possible for the transducers to be advanced each time over for example one degree in tangential direction 66 and then to be stopped. When they are stationary, the above-mentioned measurements with the transducers of the first set, the second set and third set can be carried out. After the above-mentioned measurements have been carried out, the transducers can then be moved for example one degree further. Thereupon, when the transducers are stationary again, the above-mentioned measurements with the first set, the second set and third set of transducers can be carried out again. This may be reiterated until at least a round of 360 degrees has taken place. It is important here that a beam width of the transmitted sound in the tangential direction 66 is preferably greater than the step of e.g. one degree for each of the transducers of the first set, the second set and third set, so that the beams of the successive measurements overlap. Such variants are each understood to fall within the framework of the invention.

When thus a weld has been inspected, the motor 56 can be stopped. In some situations it can be required to perform additional scans, possibly with somewhat different settings, at part of the circumferential position e.g. at the location of a detected indication. It is also possible to move the tool a short distance, for example 5 mm, in the axial direction of the pipeline to perform an additional circumferential scan to obtain more information of the same area or weld. This is all possible for a cable operated tool where the operator can decide to do so before moving to the next area or weld. When all scans for a weld are performed, the rods 46, 48, 50 will be shortened so that the transducers of the first set, the second set and third set are moved in radial direction 78 away from the wall of the pipeline and thus come off the interior surface of the pipeline. After this, the operator can transport the transport device further in the transport direction 4 again, while, using the fifth set of transducers, a next weld is located as described hereinbefore.

Incidentally, it is also possible to carry out locating of a weld as follows. First of all, a weld is located with the aid of the fifth set of transducers as described hereinbefore. An operator then has the transport device move further until the respective weld is also located with the fourth set of transducers. This affords an operator extra certainty that a weld is indeed present. Thereupon he stops the transport device and has it move backward against the transport direction 4, so that the fourth set of transducers locates the weld again. After this, the operator moves the transport device, such that the weld is positioned exactly in the middle between the fourth and fifth sets of transducers. This has as a consequence that, as discussed above, the transducers 22a, 24a, 26a come to lie on a left-hand side of the respective weld while the transducers 22b, 24b and 26d come to lie on a right-hand side of the weld. Such variants are each understood to fall within the scope of the invention.

The invention claimed is:

1. A system for inspecting a pipeline possibly filled with a fluid such as water and/or oil with ultrasound, provided with a transport device arranged to move in a transport direction of the transport device through the pipeline and a plurality of transducers for transmitting ultrasound and for receiving reflections and/or refractions of the transmitted ultrasound on a wall of the pipeline for performing a measurement and a transmitting and receiving device connected with the transducers for activating the transducers for transmitting the ultrasound and for generating receive signals respectively representing ultrasound including reflections and/or refractions received with the transducers, wherein the transducers and the transmitting and receiving device are mounted on the transport device, characterized in that the transducers are provided with a first set of transducers which comprises at least two phased array transducers staggered with respect to each other at least in the transport direction, a second set of transducers which comprises at least two transducers staggered with respect to each other in the transport direction for performing a TOFD measurement and a third set of transducers which comprises at least two transducers staggered with respect to each other in the transport direction for performing a measurement with creep waves, wherein the system is arranged to move the first set of transducers, the second set of transducers and the third set of transducers in a tangential direction with respect to the transport direction along an interior surface of a wall of the pipeline, preferably along at least a full revolution, more preferably along a loop fully closed upon itself, as a circle, and wherein the system is arranged to bring the transducers of the first set, the second set and the third set into contact with the interior surface of the pipeline during the performance of a measurement.

2. The system according to claim 1, characterized in that the system is arranged to move the first set of transducers, the second set of transducers and the third set of transducers in a tangential direction with respect to the transport direction along the interior surface of the pipeline while these transducers are in contact with this interior surface and/or that the transport device is provided with means to provide a fluid between the interior surface of the pipeline on the one hand and the transducers of the first, second and third set on the other hand.

3. The system according to claim 1, characterized in that the system is so arranged that the first set of transducers, the second set of transducers and the third set of transducers during the performance of the measurement are stationary with respect to the interior surface of the pipeline on which measurement is performed wherein preferably the system is so arranged that the first set of transducers, the second set of transducers and the third set of transducers, after the performance of the measurement, are moved in the tangential direction and stopped for the performance of a new measurement.

4. The system according to claim 1, characterized in that the system is so arranged that the first set of transducers, the second set of transducers and the third set of transducers during the performance of the measurement move in the tangential direction.

5. The system according to claim 1, characterized in that for the at least two transducers of the first set of transducers, the second set of transducers and the third set of transducers, it holds that they are staggered over a distance which is in line with predetermined codes and regulations.

6. The system according to claim 1, characterized in that the system is further provided with at least two transducers which are fixedly connected with the transport device and which are separated at a distance from each other in the transport direction.

7. The system according to claim 1, characterized in that the system is further provided with a fourth set of transducers and a fifth set of transducers, which transducers are each fixedly connected with the transport device, wherein the fourth set of transducers comprises at least two transducers which have a mutually different tangential position and which are so mounted that they transmit ultrasound in a radial direction with respect to the transport direction and wherein the fifth set of transducers comprises at least two transducers which have a mutually different tangential position and which are so mounted that they transmit ultrasound in a radial direction with respect to the transport direction, wherein the transducers of the fourth set on the one hand and the transducers of the fifth set on the other hand are separated at a distance from each other in the transport direction.

8. The system according to claim 7, characterized in that the fourth set of transducers comprises at least three transducers which are distributed in tangential direction at least substantially uniformly along a circle.

9. The system according to claim 7, characterized in that the fifth set of transducers comprises at least three transducers which are distributed in tangential direction at least substantially uniformly along a circle.

10. The system according to claim 1, characterized in that, the system is arranged such that, in use, with the first set of transducers a TANDEM and a Pulse-echo measurement, respectively, is carried out.

11. The system according to claim 10, characterized in that, the system is arranged such that, in use, with the first set of transducers also a Sector-scan measurement is carried out.

12. The system according to claim 1, characterized in that the system is further provided with a signal processing unit which is connected with the transmitting and receiving device for combined processing of receive signals coming from the first set of transducers, the second set of transducers and the third set of transducers for inspecting the pipeline, in particular for detecting a crack and/or determining the size of a crack in the wall of the pipeline and/or in a weld of the pipeline.

13. The system according to claim 1, characterized in that the signal processing unit is separated from the transport device and wherein preferably the system is further provided with at least one A/D-converter via which the transmitting and receiving device is connected with the signal processing unit wherein the A/D-converter is mounted on the transport device or is separate from the transport device.

14. The system according to claim 7, characterized in that the signal processing unit, in use, on the basis of receive signals coming from the fourth and fifth set of transducers, determines a position of the transport device with respect to the pipeline and/or determines a thickness of the wall of the pipeline and/or determines an internal profile of the wall of the pipeline.

15. The system according to claim 12, characterized in that the signal processing unit is arranged to locate a weld in the pipeline on the basis of receive signals coming from the fourth and/or fifth set of transducers.

16. The system according to claim 12, characterized in that the signal processing unit is provided with a display for real-time imaging an image representing at least a part of the receive signals.

17. The system according to claim 1, characterized in that inspecting the pipeline comprises detecting a crack in the pipeline and/or determining the size of a crack in the pipeline.

18. The system according to claim 1, characterized in that inspecting the pipeline comprising detecting a crack in a weld of the pipeline and/or determining the size of a crack in a weld of the pipeline.

19. The system according to claim 1, characterized in that the middle between the first set of transducers, the middle between the second set of transducers and the middle between the third set of transducers are each situated at least substantially in a same flat plane which is directed perpendicular to the transport direction of the transport device.

20. The system according to claim 1, characterized in that the first set of transducers, the second set of transducers and the third set of transducers are arranged in the tangential direction at least substantially uniformly distributed along a circle.

21. The method for inspecting a pipeline possibly filled with a fluid such as water and/or oil with a system according to claim 1, characterized in that the following steps are carried out:
   a. the transport device is transported in the transport direction through the pipeline to a part of the pipeline to be inspected and is stopped at the part to be inspected;
   b. the transducers of the first set, the transducers of the second set and the transducers of the third set are brought into contact with an interior surface of a wall of the pipeline;
   c. using the transducers of the first set, ultrasound is transmitted and receive signals are generated while the transducers of the first set are in contact with the interior surface of the pipeline;
   d. using the transducers of the second set, ultrasound is transmitted and receive signals are generated while the transducers of the second set are in contact with the interior surface of the pipeline;
   e. using the transducers of the third set, ultrasound is transmitted and receive signals are generated while the transducers of the third set are in contact with the interior surface of the pipeline;
   f. the first set of transducers, the second set of transducers and the third set of transducers are moved in a tangential direction with respect to the transport direction along the interior surface of the pipeline.

22. The method according to claim 21, characterized in that step f is carried out while the transducers of the first set of transducers, the transducers of the second set and the transducers of the third set are in contact with this interior surface and/or that between the interior surface and the transducers of the first, second and third set a fluid is provided.

23. The method according to claim 21, characterized in that during the carrying out of step c, step d and step e the first set of transducers, the second set of transducers and the third set of transducers are stationary with respect to the interior surface of the pipeline.

24. A The method according to claim 23, characterized in that after carrying out step f, in a step g the first set of transducers, the second set of transducers and the third set of transducers are stopped.

25. The method according to claim 24, characterized in that step b, step c and step d are carried out in a step h, with step h, step f and step g being successively carried out repeatedly.

26. The method according to claim 21, characterized in that step c, step d, and step e are carried out in a step h and that step h and step f are carried out simultaneously.

27. The method according to claim 21, characterized in that in step d with the first set of transducers, a TANDEM measurement and a Pulse-echo measurement, respectively, is carried out.

28. The method according to claim 27, characterized in that in step d with the first set of transducers a Sector scan measurement is carried out.

29. The method according to claim 21, characterized in that using a fourth set of transducers and fifth set of transducers, a position of the transport device with respect to the pipeline is determined and/or a thickness of the wall of the pipeline is determined.

30. The method according to claim 29, characterized in that by using the fourth set of transducers and/or the fifth set of transducers welds in the pipeline are located during the carrying out of step a.

31. The method according to claim 21, characterized in that the receive signals coming from the first set of transducers, the second set of transducers and the third set of transducers are processed in combination for obtaining an inspection result.

32. The method according to claim 21, characterized in that on a display an image is imaged which represents at least a part of the receive signals.

33. The method according to claim 21, characterized in that inspecting the pipeline comprises detecting a crack in the pipeline and/or determining the size of a crack in the wall of the pipeline.

34. The method according to claim 21, characterized in that inspecting the pipeline comprises detecting a crack in a weld of the pipeline and/or determining the size of a crack in a weld of the pipeline.

* * * * *